United States Patent [19]

Chou

[11] Patent Number: 5,648,473
[45] Date of Patent: Jul. 15, 1997

[54] 2'-DEOXY-2', 2'-DIFLUOROPYRIMIDINE NUCLEOSIDES AND 2'-DEOXY-2'-FLUOROPYRIMIDINE NUCLEOSIDES AND INTERMEDIATES

[75] Inventor: Ta-Sen Chou, Indianapolis, Ind.

[73] Assignee: Eli Lilly and Company, Indianapolis, Ind.

[21] Appl. No.: 454,447

[22] Filed: May 30, 1995

Related U.S. Application Data

[60] Division of Ser. No. 44,345, Apr. 7, 1993, Pat. No. 5,594,124, which is a continuation-in-part of Ser. No. 902,313, Jun. 22, 1992, abandoned.

[51] Int. Cl.$^6$ .............................. C07H 15/00; C07G 3/00
[52] U.S. Cl. ..................... 536/18.4; 536/4.1; 536/18.5
[58] Field of Search ............................ 536/4.1, 18.5, 536/18.4

[56] References Cited

U.S. PATENT DOCUMENTS

| 3,282,921 | 11/1966 | Verheyden et al. | 260/211 |
|---|---|---|---|
| 4,145,531 | 3/1979 | Eckstein et al. | 536/26 |
| 4,211,773 | 7/1980 | Lopez et al. | 424/180 |
| 4,526,988 | 7/1985 | Hertel | 549/313 |
| 4,625,020 | 11/1986 | Brundidge et al. | 536/18 |
| 4,751,221 | 6/1988 | Watanabe et al. | 514/46 |
| 4,965,374 | 10/1990 | Chou et al. | 549/313 |

FOREIGN PATENT DOCUMENTS

| 145978 | 6/1985 | European Pat. Off. . |
|---|---|---|
| 211354 | 2/1987 | European Pat. Off. . |
| 219829 | 4/1987 | European Pat. Off. . |
| 339161 | 11/1989 | European Pat. Off. . |
| 345751 | 12/1989 | European Pat. Off. . |
| 428109 | 5/1991 | European Pat. Off. . |
| 2125401 | 3/1984 | United Kingdom . |

OTHER PUBLICATIONS

Vorbuggen, et al., *J. Org. Chem.*, 41(12), 2084–86 (1976).
Hubbard, et al., *Nucleic Acid Research*, 12(17), 6827–37 (1984).
R. P. Hodge, et al., *J. Org. Chem.*, 56, 1553–64 (1991).
Tann, et al., *J. Org. Chem.*, 50, 3644–47 (1985).
Howell, et al., *J. Org. Chem.*, 53, 85–88 (1988).
Hertel, et al., *J. Org. Chem.*, 53(11), 2406–09 (1988).
Fox, et al., *Int. Symposium of Med. Chem. 7th*, 27–39 (1980).
Hoffer, *Chem. Ber.*, 93, 2777–81 (1960).

*Primary Examiner*—James O. Wilson
*Attorney, Agent, or Firm*—Margaret M. Brumm

[57] ABSTRACT

A stereoselective glycosylation process for preparing beta-anomer enriched 2'-deoxy-2',2'-difluoropyrimidine nucleosides and 2'-deoxy-2'-fluoropyrimidine nucleosides which involves reacting an alpha-anomer enriched 2-deoxy-2,2-difluorocarbohydrate or 2-deoxy-2-fluorocarbohydrate with at least a molar equivalent of a pyrimidine nucleobase derivative in a low freezing inert solvent.

9 Claims, No Drawings

2'-DEOXY-2', 2'-DIFLUOROPYRIMIDINE NUCLEOSIDES AND 2'-DEOXY-2'-FLUOROPYRIMIDINE NUCLEOSIDES AND INTERMEDIATES

CROSS REFERENCE TO RELATED APPLICATIONS

This application is a divisional of application Ser. No. 08/044,345, filed Apr. 7, 1993, now U.S. Pat. No. 5,594,124, which is a continuation-in-part of application Ser. No. 07/902,313, filed Jun. 22, 1992, now abandoned.

BACKGROUND OF THE INVENTION

1. Field of the Invention

The invention pertains to the field of pharmaceutical chemistry and provides a stereoselective glycosylation process for preparing 2'-deoxy-2',2'-difluoropyrimidine nucleosides and 2'-deoxy-2'-fluoropyrimidine nucleosides.

2. State of the Art

The continued interest in the synthesis of 2'-deoxynucleosides and their analogues is reflected in their successful use as therapeutic agents in viral and cancerous diseases. A critical step in the synthesis of 2'-deoxynucleosides is the condensation of the nucleobase and carbohydrate to form the N-glycosidic bond. When the carbohydrate possesses a 2-hydroxy substituent, the substituent provides a substantial degree of 1,2-anchiomeric assistance, which facilitates stereoselective glycosylation. However, processes for synthesizing of 2'-deoxynucleosides are typically non-stereoselective and form a mixture of alpha and beta nucleosides.

Vorbruggen, et al., *J. Org. Chem.*, 41, 2084 (1976) provided an outstanding development in the field of glycosylation and showed how nucleosides may be obtained from the Friedel-Crafts catalyzed reaction of a peracylated carbohydrate and silylated heterocycles in a solvent such as 1,2-dichloroethane or acetonitrile. But when this process was applied to the synthesis of 2'-deoxynucleosides, a 1:1 alpha to beta-anomeric mixture of nucleoside products was produced.

Some deoxynucleosides have been prepared in high yield from deoxyhalogenose with Friedel-Crafts catalysts, notably, 1-chloro-2-deoxy-3,5-di-p-toluoyl-alpha-D-erythro-pentofuranose; see, M. Hofer, *Chem. Ber*, 93, 2777 (1960). However, halogenoses are less stable thermally than peracylated carbohydrates and produce a 1:1 alpha to beta-anomeric mixture of nucleoside products. Walker, et al., *Nucleic Acid Research*, 12, 6827 (1984), used halogenose in condensation reactions to study the factors controlling the anomeric ratio of nucleoside products and found that beta-anomer nucleosides were formed exclusively from alpha-halo-carbohydrates via $S_N2$ displacement. The corresponding alpha-anomer nucleoside contamination was determined to result from the anomerization of alpha-halo carbohydrate to beta-halo carbohydrate before the $S_N2$ displacement reaction occurs. Walker, et al., found that by changing the solvent or catalyst higher yields of the desired beta-anomer nucleoside were produced.

R. P. Hodge et. al., *J. Org. Chem.*, 56, 1553 (1991), described preparing pyrimidine and purine nucleosides containing deuterium at the C-1' position by the method described by Walker, et al. 1'-Deuterium-2'-deoxycytidine was prepared by reacting a carbohydrate and silylated cytosine derivative but the reaction gave poor yields. However, the yield was significantly improved when silylated uridine derivatives were used.

The synthesis of 2'-deoxy-2'-fluoronucleosides advanced rapidly when a procedure for synthesizing 2-deoxy-2-fluoro-3,5-di-O-benzoyl-alpha-D-arabinosyl bromide was made available; see Tann, et. al., *J. Org. Chem.*, 50, 3644 (1985) and Howell, et. al., *J. Org. Chem.*, 53, 85 (1988). It was discovered that 2-deoxy-2-fluoro-3,5-di-O-benzoyl-alpha-D-arabinosyl bromide did not anomerize in dry acetonitrile over extended periods. Therefore, high yields of beta-nucleosides could be obtained from 2-deoxy-2-fluoro-3,5-di-O-benzoyl-alpha-O-arabinosyl bromide via $S_N2$ displacement. Also, stereoselectivity of the nucleoside products could be achieved if either carbon tetrachloride or chloroform solvents was employed.

The formation of the N-glycoside bond in 2'-deoxy-2',2'-difluoronucleoside synthesis is much more difficult than in instances where the carbohydrate is 1,2-anchiomericly assisted or contains only 1 fluorine at the C-2 position. The traditional carbohydrate leaving groups, such as those used in the Vorbruggen condensation method, acetate, chloride and bromide, render the carbohydrate inactive. In order to overcome this problem, Hertel, U.S. Pat. No. 4,526,988, described a modified version of the Vorbruggen condensation method that relied on more reactive sulfonate leaving groups being attached to the carbohydrate to affect its reactivity. For example, hydroxy protected carbohydrates, such as 2-deoxy-2,2-difluoro-D-ribofuranose, containing methanesulfonate, toluenesulfonate, ethanesulfonate, isopropanesulfonate or 4-methoxybenzenesulfonate as a leaving group at the C-1 position, were reacted with a protected nucleobase at temperatures of 50° C. to 220° C., in the presence of a high boiling solvent, such as dimethylformamide, dimethylacetamide and hexamethylphosphoramide. Hertel teaches that when carrying out the glycosylation reaction at elevated pressures, any convenient inert solvent, such as ethers, halogenated alkanes, and aromatics, can be used since the elevated pressure eliminates the loss of low boiling inert solvents due to evaporation. However, at reaction temperatures from room temperature to 100° C., a catalyst such as trifluoromethanesulfonyloxysilane is required.

U.S. Pat. No. 4,965,374, Chou, et al., reports that Hertel's condensation method provides alpha-anomer stereoselectively in a 4:1 alpha to beta anomeric ratio of nucleoside products and goes on to describe an improved procedure, based on the Vorbruggen condensation method, that employs a pivotol intermediate of 2-deoxy-2,2-difluoro-3,5-di-O-benzoyl-alpha-D-arabinosyl methanesulfonate. However, Chou's condensation method forms a 1:1 alpha to beta anomer mixture of nucleoside products.

Despite the preceding advances in nucleoside synthesis, there continues to be a need for a stereoselective glycosylation process capable of efficiently producing beta-anomer enriched 2'-deoxy-2',2'-difluoropyrimidine nucleosides and 2'-deoxy-2'-fluoropyrimidine nucleosides in high yield and in the absence of a catalyst for reactive and relatively unreactive nucleobase derivatives.

Accordingly, one object of the present invention is to provide a stereoselective glycosylation process for preparing beta-anomer enriched 2'-deoxy-2',2'-difluoropyrimidine nucleosides and 2'-deoxy-2'-fluoropyrimidine nucleosides at reaction temperatures below 50° C.

Another object of the present invention is to provide a stereoselective glycosylation process for preparing beta-anomer enriched 2'-deoxy-2',2'-difluoropyrimidine nucleosides and 2'-deoxy-2'-fluoropyrimidine nucleosides without the use of a catalyst.

Another object of the present invention is to provide a stereoselective glycosylation process for preparing beta-anomer enriched 2'-deoxy-2',2'-difluoropyrimidine nucleosides and 2'-deoxy-2'-fluoropyrimidine nucleosides capable of employing reactive and relatively unreactive nucleobase derivatives.

Another object of the present invention is to provide a stereoselective glycosylation process for preparing beta-anomer enriched 2'-deoxy-2',2'-difluoropyrimidine nucleosides and 2'-deoxy-2'-fluoropyrimidine nucleosides in yields higher than those produced by conventional glycosylation procedures.

Yet another object of the present invention is to provide a stereoselective glycosylation process for preparing beta-anomer enriched 2'-deoxy-2',2'-difluoropyrimidine nucleosides and 2'-deoxy-2'-fluoropyrimidine nucleosides offering a means for isolating beta-anomer enriched nucleosides in the form of a crude product or acid addition salt, such as a hydrochloride salt.

Other objects and advantages of the present invention will become apparent from the following description of embodiments.

SUMMARY OF THE INVENTION

The invention is a stereoselective glycosylation process for preparing a beta-anomer enriched nucleoside of the formula

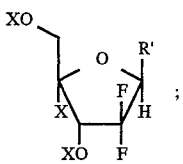
(I)

wherein each X is independently selected from hydroxy protecting groups and R' is a nucleobase selected from the group consisting of

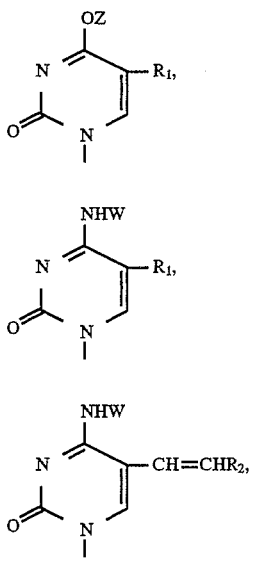

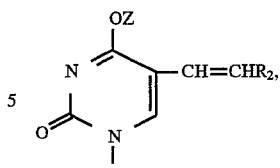

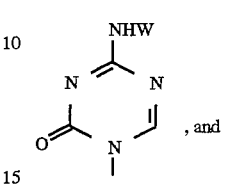

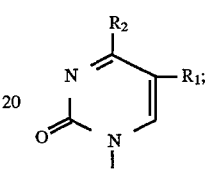

wherein $R_1$ is selected from the group consisting of hydrogen, alkyl, substituted alkyl and halo; $R_2$ is selected from the group consisting of hydrogen, alkyl and halo; Z is a hydroxy protecting group and W is an amino protecting group; comprising reacting an alpha-anomer enriched 2,2-difluorocarbohydrate of the formula

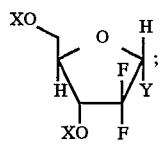
(II)

wherein Y is selected from the group consisting of trifluoromethanesulfonyloxy, 1,1,1-trifluoroethanesulfonyloxy octafluorobutanesulfonyloxy and nonafluorobutanesulfonyloxy and X is as defined above; with at least a molar equivalent of a nucleobase derivative, R", selected from the group consisting of

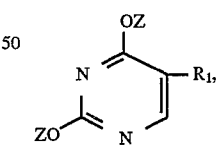

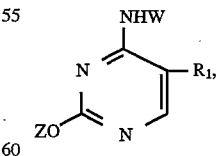

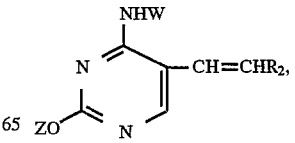

-continued

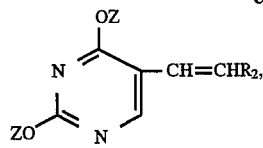

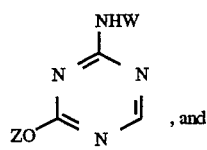, and

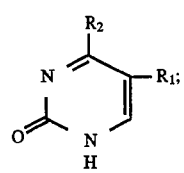

wherein R₁, R₂, Z and W are as defined above; in a low freezing inert solvent.

In another aspect, the invention is a stereoselective process for preparing an alpha-anomer enriched 2,2-difluorocarbohydrate of formula II comprising reacting a lactol of the formula

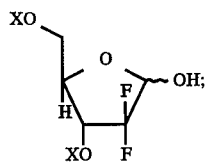 (III)

wherein X is as defined above; with a base in a low freezing inert solvent; adjusting the temperature of the reaction mixture from about −40° C. to about −120° C.; and adding a sulfonating reagent.

In another aspect, the invention is the alpha-anomer enriched 2,2-difluorocarbohydrate of formula II.

In another aspect, the invention is a stereoselective glycosylation process for preparing a beta-anomer enriched nucleoside of the formula

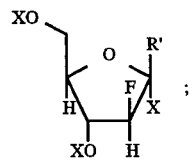 (IV)

wherein X and R' are as defined above; comprising reacting an alpha-anomer enriched 2-fluorocarbohydrate of the formula

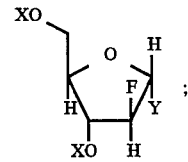 (V)

wherein Y and X are as defined above; with at least a molar equivalent of a nucleobase derivative, R", wherein R" is as defined above; in a low freezing inert solvent.

In another aspect, the invention is a stereoselective process for preparing an alpha-anomer enriched carbohydrate of the formula V comprising reacting a 2-fluorolactol of the formula

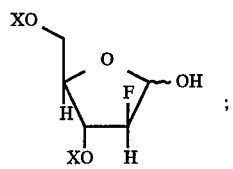

wherein X is as defined above; with a base in a low freezing inert solvent; adjusting the temperature of the reaction mixture from about −40° C. to about −120° C.; and adding a sulfonating reagent.

In yet another aspect, the invention is the alpha-anomer enriched 2-fluorocarbohydrate of formula V.

This invention also provides a stereoselective glycosylation process for preparing a beta-anomer enriched nucleoside of the formula

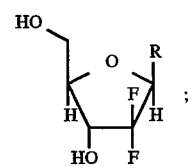 (VII)

wherein R is a deblocked nucleobase selected from the group consisting of

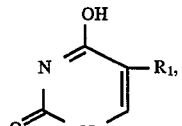

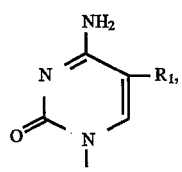

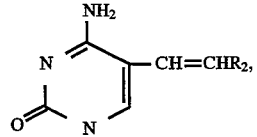

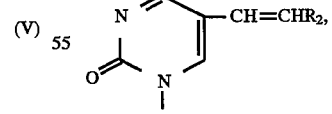

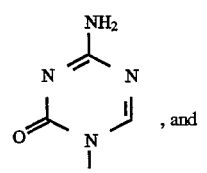, and

-continued

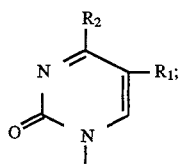

wherein R₁ is selected from the group consisting of hydrogen, alkyl, substituted alkyl and halo; R₂ is selected from the group consisting of hydrogen, alkyl and halo; comprising reacting an alpha-anomer enriched 2,2-difluorocarbohydrate of the formula

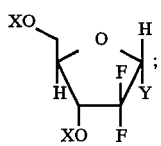 (II)

wherein Y is selected from the group consisting of trifluoromethanesulfonyloxy, 1,1,1-trifluoroethanesulfonyloxy, octafluorobutanesulfonyloxy and nonafluorobutanesulfonyloxy and X is a hydroxy protecting group; with at least a molar equivalent of a nucleobase derivative, R"; wherein R" is as defined above; in a low freezing inert solvent; and deblocking.

Also provided is a stereoselective glycosylation process for preparing a beta-anomer enriched nucleoside of the formula

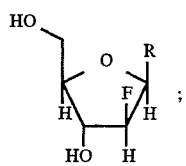 (VIII)

wherein R is a deblocked nucleobase as defined above; comprising reacting an alpha-anomer enriched 2-fluorocarbohydrate of the formula

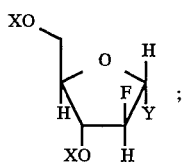 (V)

wherein Y is selected from the group consisting of trifluoromethanesulfonyloxy, 1,1,1-trifluoroethanesulfonyloxy, octafluorobutanesulfonyloxy and nonafluorobutanesulfonyloxy and X is a hydroxy protecting group; with at least a molar equivalent of a nucleobase derivative, R"; wherein R" is as defined above; in a low freezing inert solvent; and deblocking.

DETAILED DESCRIPTION OF THE INVENTION

Throughout this document, all temperatures are in degrees Celsius, all proportions, percentages and the like, are in weight units and all mixtures are in volume units, except where otherwise indicated. Anomeric mixtures are expressed as a weight/weight ratio or as a percent.

The term "xylenes" alone or in combination refers to all isomers of xylene and mixtures thereof. The term "lactol" alone or in combination refers to a 2-deoxy-2,2-difluoro-D-ribofuranose or 2-deoxy-2-fluoro-D-ribofuranose. The term "carbohydrate" alone or in combination refers to an activated lactol wherein the hydroxy group at the C-1 position has been replaced by a desirable leaving group. The term "halo" alone or in combination refers to chloro, iodo, fluoro and bromo. The term "alkyl" alone or in combination refers to straight, cyclic and branched chain aliphatic hydrocarbon groups which preferably contain up to 7 carbon atoms, such as methyl, ethyl, n-propyl, isopropyl, n-butyl, t-butyl, n-pentyl, n-hexyl, 3-methylpentyl groups and the like or substituted straight, cyclic and branched chain aliphatic hydrocarbons, such as chloroethyl, 1,2-dichloroethyl, and the like. The term "alkoxy" alone or in combination refers to the general formula AO; wherein A is alkyl. The term "aryl" alone or in combination refers to carbocyclic or heterocyclic groups such as phenyl, naphthyl, thienyl and substituted derivatives thereof. The term "thioalkyl" alone or in combination refers to the general formula BS; wherein B is alkyl or hydrogen. The term "ester" alone or in combination refers to the general formula EOOC; wherein E is alkyl or aryl. The term "aromatic" alone or in combination refers to benzene like structures containing $(4\pi+2)$ delocalized electrons. The terms "sulfonate" or "sulfonyloxy" alone or in combination refer to the general formula $GSO_3$; wherein G is alkyl or aryl. The term "substituted" alone or in combination refers to substitution by at least one or more of the groups selected from cyano, halo, carboalkoxy, aryl, nitro, alkoxy and dialkylamino. The phrase "anomer enriched" alone or in combination refers to an anomeric mixture wherein the ratio of a specified beta- or alpha-anomer is greater than 1:1 and includes a substantially pure anomer.

In accordance with the present glycosylation process, beta-anomer enriched 2'-deoxy-2',2'-difluoronucleosides and 2'-deoxy-2'-fluoronucleosides are prepared by reacting an alpha-anomer enriched carbohydrate of formulas II and V with at least a molar equivalent of a protected nucleobase derivative in a low freezing inert solvent as shown in the following reaction schemes:

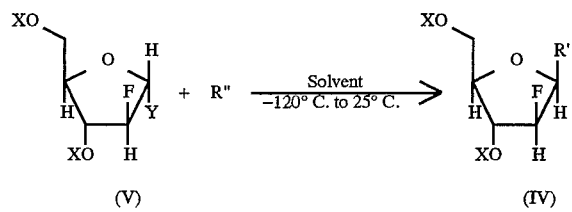

and

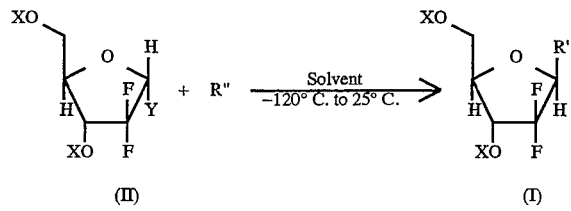

wherein X, Y, R" and R' are as defined above. While not wishing to be bound by theory, it is believed that the glycosylation reaction proceeds primarily via $S_N2$ displacement. Therefore, the beta-anomer enriched nucleoside products are derived from alpha-anomer enriched carbohydrates.

The lactol starting materials suitable for use in the present glycosylation process are commonly known in the art and can be readily synthesized by standard procedures commonly employed by those of ordinary skill in the art. For example, U.S. Pat. No. 4,526,988 teaches the synthesis of a 2-deoxy-2,2-difluoro-D-ribofuranose of formula III and Reichman, et al., *Carbohydr. Res.*, 42, 233 (1975) teaches the synthesis of a 2-deoxy-2-fluoro-D-ribofuranosyl of the formula VI. In a preferred embodiment of the present invention, 2-deoxy-2,2-difluoro-D-ribofuranose-3,5-dibenzoate of formula III is used to prepare blocked nucleoside products.

Glycosylation reactions typically require protecting the oxygen atoms of the hydroxy groups of the lactol of formulas III and VI to prevent the hydroxy groups from reacting with the nucleobase derivative, or being decomposed in some manner. Hydroxy protecting groups (X) suitable for use in the present glycosylation process may be chosen from known protecting groups used in synthetic organic chemistry. Each hydroxy protecting group selected is preferably capable of being efficiently placed on the lactol and easily removed therefrom once the glycosylation reaction is complete. Hydroxy protecting groups known in the art are described in Chapter 3 of *Protective Groups in Organic Chemistry*, McOmie Ed., Plenum Press, New York (1973) and Chapter 2 of *Protective Groups in Organic Synthesis*, Green, John, J. Wiley and Sons, New York (1981); preferred are ester forming groups such as formyl, acetyl, substituted acetyl, propionyl, butynyl, pivaloyl, 2-chloroacetyl, benzoyl, substituted benzoyl, phenoxycarbonyl, methoxyacetyl; carbonate derivatives such as phenoxycarbonyl, ethoxycarbonyl, t-butoxycarbonyl, benzyloxycarbonyl; alkyl ether forming groups such as benzyl, diphenylmethyl, triphenylmethyl, t-butyl, methoxymethyl, tetrahydropyranyl, allyl, tetrahydrothienyl, 2-methoxyethoxy methyl; and silyl ether forming groups such as trialkylsilyl, trimethylsilyl, isopropyldialkylsilyl, alkyldiisopropylsilyl, triisopropylsilyl, t-butyldialkylsilyl and 1,1,3,3-tetraisopropyldisloxanyl; carbamates such as N-phenylcarbamate and N-imidazoylcarbamate; however more preferred are benzoyl, mono-substituted benzoyl and disubstituted benzoyl, acetyl, pivaloyl, triphenylmethyl ethers, and silyl ether forming groups, especially t-butyldimethylsilyl; while most preferred is benzoyl.

In attaching each hydroxy protecting group to the lactol typical reactions conditions are employed and depend on the nature of the protecting group chosen. Typical reaction conditions are described in U.S. Pat. No. 4,526,988, which is incorporated herein by reference.

To obtain an efficient reaction of the nucleobase derivative and carbohydrate, an appropriate leaving group is stereoselectively attached to the lactol of formulas III and VI which activates the lactol and generates the alpha-anomer enriched carbohydrate of formulas II and V. The leaving group (Y) of the carbohydrate may be selected from the group consisting of trifluoromethanesulfonyloxy, 1,1,1-trifluoroethanesulfonyloxy, octafluorobutanesulfonyloxy ($C_4F_8HSO_3$) and nonafluorobutanesulfonyloxy ($C_4F_9SO_3$); more preferred is trifluoromethanesulfonyloxy.

The alpha-anomer enriched carbohydrate of formulas II and V are prepared by reacting the lactol of formulas III and VI with an amine base such as triethylamine, trimethylamine, tributylamine, dibutylamine, diethylmethylamine, dimethylethylamine, benzylmethylamine, N-methylmorpholine, tripropylamine, dipropylethylamine, N,N-dimethylbenzylamine, diisopropylethylamine, diethylamine, 1,8-diazabicyclo[5.4.0]undec-7-ene and 1,5-diazabicyclo[4.3.0]non-5-ene. However, the use of secondary amine bases may interfere with subsequent sulfonation, therefore care must be taken to limit reaction time and maintain low temperatures when secondary amine bases are employed. The amine base preferably has a pKa of from about 8 to about 20 and is employed in a range of from about 1 molar equivalent to about 2 molar equivalents and more preferably from about 1.2 molar equivalents to about 1.5 molar equivalents. The reaction is carried out in an inert solvent having a freezing point temperature preferably below $-78°$ C. Preferred solvents are selected from the group consisting of dichloromethane, 1,2-dichloroethane, dichlorofluoromethane, acetone, toluene, anisole, chlorobenzene, and mixtures thereof. The temperature of the solvent mixture is adjusted preferably in the range from about $-40°$ C. to about $-120°$ C. and more preferably below about $-78°$ C. While not wishing to be bound by theory it is believed that the low temperature shifts the alpha to beta anomeric ratio of the lactol in favor of the alpha-anomer in a range from about 2:1 to about 4:1 alpha to beta. For example, a compound of formula III, where X is benzoyl, was added to dichloromethane and triethylamine at room temperature for 30 minutes. Next, the temperature of the solvent mixture was lowered. A $^{19}F$ NMR, taken at the various temperatures, showed an increase in the alpha to beta ratio of the ionized lactol as the temperature was lowered:

| Temperature | Alpha/Beta Ratio |
| --- | --- |
| 19° C. | 2.0:1 |
| −3° C. | 2.3:1 |
| −23° C. | 2.5:1 |
| −43° C. | 3.0:1 |
| −63° C. | 3.6:1 |
| −83° C. | 4.4:1 |

The ionized lactol is then trapped in solution at the low temperature and higher alpha-anomer ratio by adding a sulfonating reagent which forms an alpha-anomer enriched carbohydrate.

The sulfonating reagents are selected from the group consisting of trifluoromethanesulfonyl anhydride, trifluoromethanesulfonyl halide, 1,1,1-trifluoroethanesulfonyl halide, 1,1,1-trifluoroethanesulfonyl anhydride, octaflic acid halide, octaflic acid anhydride, nonaflic acid halide and nonaflic acid anhydride, depending on the leaving group desired; more preferred is trifluoromethanesulfonyl anhydride. The alpha-anomer enriched carbohydrates prepared from the ionized lactol, especially carbohydrates containing trifluoromethanesulfonyloxy, are unstable at room temperature and therefore are preferably used in-situ. Also, due to the reactivity of the sulfonating reagents, the glycosylation reaction may be carried out in a batch or continuous mode for large scale operations.

The pyrimidine nucleobases (R") employed herein are commonly known to organic chemist and no discussion of their synthesis is necessary. However, in order to be useful in the present glycosylation process the nucleobase derivatives (R") or their tautomeric equivalents, bearing amino or hydroxy groups preferably contain primary amino protecting groups (W) and/or hydroxy protecting groups (Z), depending on the nature of the nucleobase derivative selected. The protecting group blocks the hydroxy or amino groups which may provide a competing reaction site for the alpha-anomer carbohydrate. The protecting groups are attached to the nucleobase derivative (R') before it is reacted with the alpha-anomer enriched carbohydrate of formulas II and V and are removed subsequent thereto. A procedure for protecting the nucleobase derivatives is described in U.S. Pat. No. 4,526,988.

Preferred amino protecting groups (W) for pyrimidine nucleobase derivatives are selected from the group consisting of silyl ether forming groups such as trialkylsilyl, t-butyldialkylsilyl and t-butyldiarylsilyl; carbamates such as t-butoxycarbonyl, benzyloxycarbonyl, 4-methoxybenzyloxycarbonyl, and 4-nitrobenzyloxycarbonyl, formyl, acetyl and benzoyl; ether forming groups such as methoxymethyl, t-butyl, benzyl, allyl and tetrahydropyranyl; more preferred is trimethylsilyl. Preferred hydroxy protecting groups (Z) for pyrimidine nucleobase derivatives are selected from silyl ether forming groups trialkylsilyl carbamates such as t-butoxycarbonyl, benzyloxycarbonyl, 4-methoxybenzyloxycarbonyl and 4-nitrobenzyloxycarbonyl; carbocyclic esters such as formyl, acetyl, and pivalamido; preferred is trimethylsilyl.

In providing protective groups to the nucleobase derivatives the protecting group itself may be protected. For example, N-acetylcytosine may be protected with trimethylsilyl to form bis-trimethylsilyl-N-acetylcytosine.

In addition, it is often advisable to convert any keto oxygen atoms on the nucleobase derivative to enol form. This makes the nucleobase derivative more aromatic and enhances the reactivity of the nucleobase derivative with the alpha-anomer enriched carbohydrate of formulas II and V. It is most convenient to enolize the keto oxygens and provide silyl protecting groups for them. In a preferred embodiment of the present process the nucleobase derivative (R") is of the formula

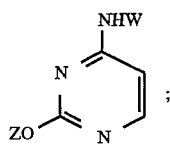

wherein Z and W are trimethylsilyl.

The reaction solvents suitable for use in the present glycosylation process must be inert to the glycosylation reaction and have a freezing point temperature from about 40° C. to about −120° C. Preferred reaction solvents are selected from the group consisting of dichloromethane, 1,2-dichloroethane, dichlorofluoromethane, acetone, toluene, anisole, chlorobenzene, and mixtures thereof; more preferred is dichloromethane.

In accordance with the present process, at least an equimolar amount of nucleobase derivative (R") must be employed relative to the amount of carbohydrate employed. However, it is more preferable to use a molar excess of nucleobase derivative in amounts greater than 1 molar equivalent to about 20 molar equivalents, depending on the nature of the nucleobase derivative selected; preferred is from about 3 equivalents to about 20 equivalents and more preferably about 20 equivalents.

Although not critical, it is advisable that the reaction between the alpha-anomer enriched carbohydrate of formulas II and V and the nucleobase derivative be carried out in a dry atmosphere, e.g. in dry air, nitrogen or argon. This is because certain nucleobase derivatives are moisture sensitive.

As mentioned above, certain alpha-anomer carbohydrates of formulas II and V are unstable at room temperature. Therefore, the glycosylation reaction is carried out at or below room temperature and more preferably carried out from about 25° C. to about −120° C. However, the glycosylation reaction temperature employed will depend on the leaving group attached to the alpha-anomer carbohydrate. For example, when the leaving group (Y) is trifluoromethanesulfonate, the preferred reaction temperature ranges from about −50° C. to about 25° C. while about −20° C. to about 23° C. is most preferred. On the other hand, when the leaving group (Y) is 1,1,1-trifluoroethanesulfonate, octaflate or nonaflate, the preferred reaction temperature ranges from about −20° C. to about 25° C. while about 0° C. to about 23° C. is most preferred. The glycosylation reaction is preferably carried out under atmospheric pressure and is substantially complete in about 5 minutes to about 1 hour.

The progress of the the present glycosylation process may be followed by procedures well known to one of ordinary skill in the art such as high pressure liquid chromatography (HPLC) and thin layer chromatography (TLC) which can be used to detect the presence of nucleoside product.

In accordance with the present glycosylation process, the beta-anomer enriched nucleosides are prepared in an anomer ratio greater than 1:1 to about 1:7 alpha to beta.

The final phase of the reaction sequence is the removal of the protecting groups X, Z and/or W from the blocked nucleoside of formula I or IV. The same anomeric ratio of unprotected nucleoside is obtained by removal of the protecting groups.

Most silyl and silyl-amino protecting groups are easily cleaved by use of a protic solvent, such as water or an alcohol. The acyl protecting groups, such as benzoyl and the acyl-amino protecting groups, are removed by hydrolysis with a strong base at a temperature from about 0° C. to about 100° C. Strong or moderately strong bases suitable for use in this reaction are bases which have a pKa (at 25° C.) of about 8.5 to about 20.0. Such bases include alkali metal hydroxides such as sodium or potassium hydroxide; alkali metal alkoxides such as sodium methoxide or potassium t-butoxide; alkali metal amides; amines such as diethylamine, hydroxylamine, ammonia and the like; and other common bases such as hydrazine and the like. At least one equivalent of base is needed for each protecting group.

The acyl protecting groups can also be removed with acid catalysts, such as methanesulfonic acid, hydrochloric acid, hydrobromic acid, sulfuric acid, or with acidic ion exchange resins. It is preferred to carry out such hydrolysis at relatively high temperature, such as the reflux temperature of the mixture, but temperatures as low as ambient may be used when particularly strong acids are used.

The removal of ether protecting groups is carried out by known methods, for example, with ethanethiol and aluminum chloride.

The t-butyldimethylsilyl protecting group requires acid conditions, such as contact with gaseous hydrogen halide, for its removal.

Removal of the protecting groups may be conveniently carried out in alcoholic solvents, especially aqueous alkanols such as methanol. However, the deblocking reaction may also be carried out in any convenient solvent, such as polyols including ethylene glycol, ethers such as tetrahydrofuran, ketones such as acetone and methyl ethyl ketone, or dimethylsulfoxide.

In a preferred embodiment, the deblocking reaction employs ammonia to remove a benzoyl hydroxy-protecting group at a temperature of about 10° C. It is preferable, however, to use an excess of base in this reaction, although the amount of excess base used is not crucial.

The resulting beta-anomer enriched nucleosides of formula VII or VIII may be extracted and/or isolated from the reaction mixture by the techniques described in U.S. Pat. No. 4,965,374, Chou, which is incorporated herein by reference.

The following examples illustrate specific aspects of the present invention and are not intended to limit the scope thereof in any respect and should not be so construed.

EXAMPLE 1

Preparation of beta-anomer enriched 1-(2'-deoxy-2', 2'-difluoro-3',5'-di-O-benzoyl-D-ribofuranosyl)-4-aminopyrimidin-2-one with 20 equivalents of bis-trimethylsilylcytosine To 5.78 g of cytosine were added 112 ml of hexamethyldisilazane and 100 mg of ammonium sulfate. The solution was heated to 115° C.–120° C. for 1 and ½ hours with stirring and the excess hexamethyldisilazane subsequently removed. The mixture was cooled to 60° C. and reconstituted in 40 ml of 1,2-dichloroethane to form a homogenous solution of bis-trimethylsilylcytosine.

To 1 g of 2-deoxy-2,2-difluoro-D-ribofuranosyl-3,5-dibenzate was added 10 ml of dichloromethane and 0.54 ml of triethylamine. This solution was stirred at 23° C. for 30 minutes, cooled to −78° C. and reacted with 0.57 ml of trifluoromethanesulfonyl anhydride, in 0.50 ml of dichloromethane, to form alpha-anomer enriched 2-deoxy-2,2-difluoro-D-ribofuranosyl-3,5-dibenzoyl-1-trifluoromethanesulfonate intermediate in solution. Care was taken to maintain the temperature of the reaction mixture below −65° C. A $^{19}F$ nuclear magnetic resonance (NMR) analysis of the alpha-anomer enriched 2-deoxy-2,2-difluoro-D-ribofuranosyl-3,5-dibenzoyl-1-trifluoromethanesulfonate intermediate at 65° C. provided the following data:

$^{19}F$ NMR (300 MHz, CDCl$_3$), δ–77 (s, 3F, CF$_3$SO$_2$—), −111 (d, J=257 Hz, 1F, alpha-anomer), −122 (d, J=242 Hz, 1F, beta-anomer), −124 (d, J=257 Hz, 1F, alpha-anomer), −126 ppm (d, J=242 Hz, 1F, beta-anomer). It should be noted that all $^{19}F$ NMR peak shifts are relative to hexafluorobenzene, which was assigned a frequency of −162.9 ppm. The $^{19}F$ NMR spectrum also indicated fluorine—proton couplings however, the nature of these couplings were not determined.

The alpha-anomer enriched 2-deoxy-2,2-difluoro-D-ribofuranosyl-3,5-dibenzoyl-1-trifluoromethanesulfonate solution was reacted with the bis-trimethylsilylcytosine solution at −65° C. and the reaction temperature was allowed to rise to 23° C. to form the titled blocked nucleoside which was confirmed by HPLC analysis. The beta to alpha anomeric ratio of the blocked nucleoside was 1.9:1.

To extract the nucleoside product from the reaction mixture, 100 ml of dichloromethane and 200 ml of 1N hydrochloric acid were added. The organic layer was separated and washed with 200 ml of 5% sodium bicarbonate. The organic layer was again separated and washed with 200 ml of saturated sodium chloride. The titled nucleoside product precipitated from the organic layer A quantitative HPLC analysis revealed a yield of blocked beta-anomer nucleoside of 42 percent. $^1H$ NMR (DMSO): δ=4.74(4'H), 4.79 (5'H), 5.84 (5H), 5.88 (3'H), 6.44 (1'H), 7.56 (NH$_2$), 7.68 (6H). $^{13}C$ NMR (DMSO): δ=63.46 (5'C), 71.80 (3'C), 75.71 (4'C), 84.64 (1'C), 95.12 (5C), 121.86 (2'C), 141.93 (6C), 154.48 (2C), 165.87 (4C).

EXAMPLE 2

Preparation of beta-anomer enriched 1-(2'-deoxy-2', 2'-difluoro-3',5'-di-O-benzoyl-D-ribofuranosyl)-4-aminopyrimidin-2-one with 20 equivalents of bis-trimethylsilylcytosine A bis-trimethylsilylcytosine solution was prepared by suspending 5.78 g of cytosine in 75 ml of dichloromethane and adding 20.57 ml of N-methyl-N-trimethylsilyltrifluoroacetamide and cooling the resulting solution to −30° C.

To 1 g of 2-deoxy-2,2-difluoro-D-ribofuranosyl-3,5-dibenzoate was added 10 ml of dichloromethane and 0.55 ml of triethylamine. This solution was stirred at 23° C. for 30 minutes, cooled to −78° C. and reacted with 0.57 ml of trifluoromethanesulfonyl anhydride in 1 ml of dichloromethane, to form alpha-anomer enriched 2-deoxy-2,2-difluoro-D-ribofuranosyl-3,5-dibenzoyl-1-trifluoromethanesulfonate in solution. Care was taken to maintain the temperature of the reaction mixture below −65° C. The alpha-anomer enriched 2-deoxy-2,2-difluoro-D-ribofuranose-3,5-dibenzoyl-1-trifluoromethanesulfonate solution was reacted with the bis-trimethylsilylcytosine solution at −30° C. to form the titled blocked nucleoside which was confirmed by HPLC analysis. The beta to alpha anomeric ratio of the blocked nucleoside was 2.3:1.

To extract the nucleoside product from the reaction mixture, 200 ml of 1N hydrochloric acid were added. The organic layer was separated and washed with 5% sodium carbonate. A quantitative HPLC analysis of the organic layer revealed a yield of blocked beta-anomer nucleoside of 45 percent.

EXAMPLE 3

Preparation of beta-anomer enriched 1-(2'-deoxy-2', 2'-difluoro-3',5'-di-O-benzoyl-D-ribofuranosyl)-4-aminopyrimidin-2-one with 20 equivalents of bis-trimethylsilylcytosine A bis-trimethylsilyl cytosine solution was prepared by the procedure described in Example 1 and cooled to −15° C.

To 1 g of 2-deoxy-2,2-difluoro-D-ribofuranosyl-3,5-dibenzate was added 10 ml of dichloromethane and 0.54 ml of triethylamine. This solution was stirred at 23° C. for 30 minutes, cooled to −78° C. and reacted with 0.57 ml of trifluoromethanesulfonyl anhydride in 0.5 ml of dichloromethane to form an alpha-anomer enriched 2-deoxy-2,2-difluoro-D-ribofuranosyl-3,5-dibenzoyl-1-trifluoromethanesulfonate in solution. Care was taken to maintain the temperature of the reaction mixture below −65° C. The alpha-anomer enriched 2-deoxy-2,2-difluoro-D-ribofuranosyl-3,5-dibenzoyl-1-trifluoromethanesulfonate solution was reacted with the bis-trimethylsilylcytosine solution at −15° C. to form the titled blocked nucleoside which was confirmed by HPLC analysis. The beta to alpha anomeric ratio of the blocked nucleoside was 2.3:1.

To extract the nucleoside product from the reaction mixture, the dichloromethane was removed and the resulting residue was reconstituted in 21 ml of anisole and 40 ml of water then heated to 90° C. The solids that formed were removed from the solution. The organic and aqueous layers were separated and the organic layer was subsequently washed with an additional 10 ml of water. The beta-anomer nucleoside product precipitated from the organic layer. A quantitative HPLC analysis revealed a yield of blocked beta-anomer nucleoside of 58 percent.

EXAMPLE 4

Preparation of beta-anomer enriched 1-(2'-deoxy-2', 2'-difluoro-3',5'-di-O-benzoyl-D-ribofuranosyl)-4-aminopyrimidin-2-one with 20 equivalents of bis-trimethylsilylcytosine A bis-trimethylsilylcytosine solution was prepared by suspending 5.78 g of cytosine in 20 ml of dichloromethane and adding 20.57 ml of N-methyl-N-trimethylsilyltrifluoroacetamide in 10 ml of dichloromethane and cooling the resulting solution to 0° C.

To 1 g of 2-deoxy-2,2-difluoro-D-ribofuranosyl-3,5-dibenzoate was added 10 ml of dichloromethane and 0.55 ml of triethylamine. This solution was stirred at 23° C. for 30 minutes, cooled to −78° C. and reacted with 0.57 ml of trifluoromethanesulfonyl anhydride in 1 ml of dichloromethane, to form alpha-anomer enriched 2-deoxy-2,2-difluoro-D-ribofuranosyl-3,5-dibenzoyl-1-trifluoromethanesulfonate in solution. Care was taken to maintain the temperature of the reaction mixture below −65° C. The alpha-anomer enriched 2-deoxy-2,2-difluoro-D-ribofuranosyl-3,5-dibenzoyl-1-trifluoromethanesulfonate solution was reacted with the bis-trimethylsilylcytosine solution at 0° C. to form the titled blocked nucleoside which was confirmed by HPLC. The beta to alpha anomeric ratio of the blocked nucleoside was 2.5:1.

To extract the nucleoside product from the reaction mixture, 250 ml of 1N hydrochloric acid were added. The organic layer was separated and washed with 200 ml of 5% sodium carbonate. A quantitative HPLC analysis of organic layer revealed a yield of blocked beta-anomer nucleoside of 49 percent.

EXAMPLE 5

Preparation of beta-anomer enriched 1-(2'-deoxy-2', 2'-difluoro-3',5'-di-O-benzoyl-D-ribofuranosyl)-4-acetamidopyrimidin-2-one with 10 equivalents of bis-trimethylsilyl-N-acetylcytosine To 4 g of N-acetylcytosine were added 56 ml of hexamethyldisilazane and 698 mg of ammonium sulfate. This solution was heated to 115° C.–120° C. for 4 hours with stirring and the excess hexamethyldisilazane was subsequently removed. The mixture was cooled to 50° C. and constituted in 50 ml of 1,2-dichloroethane. The 1,2-dichloroethane was removed and the resulting solid residue was reconstituted in 50 ml of 1,2-dichloroethane. The 1,2-dichloroethane was again removed and an oily residue formed. The oily residue was constituted in 2.5 ml 1,2-dichloroethane to form a homogenous bis-trimethylsilyl-N-acetylcytosine solution.

To 1 g of 2-deoxy-2,2-difluoro-D-ribofuranosyl-3,5-dibenzoate was added 2 ml of dry dichloromethane. This solution was cooled to −78° C. and reacted with 0.55 ml of triethylamine and 0.58 ml of trifluoromethanesulfonyl anhydride to form alpha-anomer enriched 2-deoxy-2,2-difluoro-D-ribofuranosyl-3,5-dibenzoyl-1-trifluoromethanesulfonate in solution. Care was taken to maintain the temperature of the reaction mixture below −65° C. The alpha-anomer enriched 2-deoxy-2,2-difluoro-D-ribofuranosyl-3,5-dibenzoyl-1-trifluoromethanesulfonate solution was reacted with the bis-trimethylsilyl-N-acetylcytosine solution at 23° C. The reaction mixture was stirred at −60° C. for 1 and ½ hour to form the titled blocked nucleoside which was confirmed by HPLC analysis. The beta to alpha anomeric ratio of the blocked nucleoside was 2:1.

To extract the nucleoside product from the reaction mixture, 50 ml of dichloromethane were added. The organic layer was separated and washed successively with 50 ml of 5% sodium bicarbonate then 50 ml of 1N hydrochloric acid and 50 ml of saturated sodium chloride. A quantitative HPLC analysis of the organic layer revealed a yield of blocked beta-anomer nucleoside of 15 percent.

EXAMPLE 6

Preparation of beta-anomer enriched 1-(2'-deoxy-2', 2',-difluoro-3',5'-di-O-benzoyl-D-ribofuranosyl)-4-aminopyrimidin-2-one with 20 equivalents of bis-trimethylsilylcytosine To 5.78 g of cytosine were added 112 ml of hexamethyldisilazane and 50 mg of ammonium sulfate. The mixture was heated to 115° C.–120° C. for 3 hours with stirring and the excess hexamethyldisilazane was subsequently removed. This solution was then cooled to 27° C. and a solid residue formed which was reconstituted in 35 ml of dichloromethane to form a homogenous bis-trimethylsilylcytosine solution.

To 1 g of 2-deoxy-2,2-difluoro-D-ribofuranosyl-3,5-dibenzoate were added 10 ml of dichloromethane and 0.54 ml of triethylamine. The solution was cooled to −78° C. and reacted with 0.57 ml of trifluoromethanesulfonyl anhydride, in 0.50 ml of dichloromethane, to form alpha-anomer enriched 2-deoxy-2,2-difluoro-D-ribofuranosyl-3,5-dibenzoyl-1-trifluoromethanesulfonate in solution. Care was taken to maintain the temperature of the reaction mixture below −65° C. The alpha-anomer enriched 2-deoxy-2,2-difluoro-D-ribofuranosyl-3,5-dibenzoate-1-trifluoromethanesulfonate solution was reacted with the bis-trimethylsilylcytosine solution at 27° C. to form the titled blocked nucleoside which was confirmed by HPLC analysis and indicated that 11 percent of the alpha-anomer enriched 2-deoxy-2,2-difluoro-D-ribofuranosyl-3,5-dibenzoyl-1-trifluoromethanesulfonate remained unreacted. The beta to alpha anomeric ratio of the blocked nucleoside was 2.2:1. A quantitative HPLC analysis revealed a yield of blocked beta-anomer nucleoside of 54 percent.

EXAMPLE 7

Preparation of beta-anomer enriched 1-(2'-deoxy-2', 2'-difluoro-3',5'-di-O-benzoyl-D-ribofuranosyl)-4-aminopyrimidin-2-one with 20 equivalents of bis-trimethylsilylcytosine To 5.78 g of cytosine were added 112 ml of hexamethyldisilazane and 50 mg of ammonium sulfate. This solution was heated to 115° C.–120° C. for 2 hours with stirring and the excess hexamethyldisilazane was subsequently removed. The resulting oil was cooled to 23° C. to form a solid residue which was reconstituted in 35 ml of dichloromethane to form a homogenous bis-trimethylsilylcytosine solution and cooled to 0° C.

To 1 g of 2-deoxy-2,2-difluoro-D-ribofuranosyl-3,5-dibenzoate was added 9 ml of dichloromethane and 0.54 ml of triethylamine. The solution was cooled to −78° C. and reacted with 0.57 ml of trifluoromethanesulfonyl anhydride, in 0.50 ml of dichloromethane, to form alpha-anomer enriched 2-deoxy-2,2-difluoro-D-ribofuranosyl-3,5-dibenzoyl-1-trifluoromethanesulfonate in solution. Care was taken to maintain the temperature of the reaction mixture below −65° C. The alpha-anomer enriched 2-deoxy- 2,2-difluoro-D-ribofuranosyl-3,5-dibenzoyl-1-trifluoromethanesulfonate solution was reacted with the bis-trimethylsilylcytosine solution at 23° C. to form the titled blocked nucleoside which was confirmed by HPLC analysis. The beta to alpha anomeric ratio of the blocked nucleoside was 2.2:1.

To extract the nucleoside product from the reaction mixture was washed twice with 150 ml of 1N hydrochloric acid. The organic layer was separated, washed with 150 ml of 5% sodium bicarbonate and washed again with 150 ml saturated sodium chloride. A quantitative HPLC analysis of the organic layer revealed a yield of blocked beta-anomer nucleoside of 49 percent.

EXAMPLE 8

Preparation of beta-anomer enriched 1-(2'-deoxy-2', 2'-difluoro-3',5'-di-O-benzoyl-D-ribofuranosyl)-4-aminopyrimidin-2-one with 30 equivalents of bis-trimethylsilylcytosine To 5.9 g of cytosine were added 112 ml of hexamethyldisilazane and 25 mg of ammonium sulfate. The solution was heated to 120° C.–125° C. for 3 hours with stirring and the excess hexamethyldisilazane was subsequently removed. The resulting solid residue was reconstituted in 35 ml of dichloromethane and cooled to 10° C. to form a homogenous bis-trimethylsilylcytosine solution.

To 655 mg of 2-deoxy-2,2-difluoro-D-ribofuranosyl-3,5-dibenzoate were added 0.55 ml of dichloromethane and 0.36 ml of triethylamine. The solution was stirred at 23° C. for 30 minutes, cooled to –78° C. and reacted with 0.35 ml of trifluoromethanesulfonyl anhydride, in 0.50 ml of dichloromethane, to form alpha-anomer enriched 2-deoxy-2,2-difluoro-D-ribofuranosyl-3,5-dibenzoyl-1-trifluoromethanesulfonate in solution. Care was taken to maintain the temperature of the reaction mixture below –65° C. The alpha-anomer enriched 2-deoxy-2,2-difluoro-D-ribofuranosyl-3,5-dibenzoyl-1-trifluoromethanesulfonate solution was reacted with the bis-trimethylsilylcytosine solution at 10° C. to form the titled blocked nucleoside which was confirmed by HPLC analysis. The beta to alpha anomeric ratio of the blocked nucleoside was 2.7:1. A quantitative HPLC analysis revealed a yield of blocked beta-anomer nucleoside of 60 percent.

EXAMPLE 9

Preparation of beta-anomer enriched 1-(2'-deoxy-2', 2'-difluoro-3',5'-di-O-benzoyl-D-ribofuranosyl)-4-aminopyrimidin-2-one with 20 equivalents of bis-trimethylsilylcytosine To 5.78 g of cytosine were added 112 ml of hexamethyldisilazane and 50 mg of ammonium sulfate. The solution was heated to 115° C.–120° C. for 1 and ½ hours with stirring and the excess hexamethyldisilazane was subsequently removed. The resulting solid residue was reconstituted in 40 ml of 1,2-dichloromethane at 23° C. to form a homogenous bis-trimethylsilyl cytosine solution.

To 1 g of 2-deoxy-2,2-difluoro-D-ribofuranosyl-3,5-dibenzoate was added 10 ml of dichloromethane and 1.2 ml of triethylamine. The solution was cooled to –78° C. and reacted with 0.57 ml of trifluoromethanesulfonyl anhydride, in 0.50 ml of dichloromethane, to form alpha-anomer enriched 2-deoxy-2,2-difluoro-D-ribofuranosyl-3,5-dibenzoyl-1-trifluoromethanesulfonate in solution. Care was taken to maintain the temperature of the reaction mixture below –65° C. The alpha-anomer enriched 2-deoxy-2,2-difluoro-D-ribofuranosyl-3,5-dibenzoyl-1-trifluoromethanesulfonate solution was reacted with the bis-trimethylsilylcytosine solution at 23° C. to form the titled blocked nucleoside which was confirmed by HPLC analysis. The beta to alpha anomeric ratio of the blocked nucleoside was 2.8:1. A quantitative HPLC analysis revealed a yield of blocked beta-anomer nucleoside of 50 percent.

EXAMPLE 10

Preparation of beta-anomer enriched 1-(2'-deoxy-2', 2'-difluoro-3',5'-di-O-benzoyl-D-ribofuranosyl)-4-aminopyrimidin-2-one with 20 equivalents of bis-trimethylsilylcytosine To 5.78 g of cytosine were added 112 ml of hexamethyldisilazane and 50 mg of ammonium sulfate. The mixture was heated to 115° C.–120° C. for 1 and ½ hours with stirring and the excess hexamethyldisilazane was subsequently removed. The resulting solid residue was reconstituted in 40 ml of dichloromethane at 23° C. to form a homogenous bis-trimethylsilylcytosine solution.

To 1 g of 2-deoxy-2,2-difluoro-D-ribofuranosyl-3,5-dibenzoate was added 10 ml of dichloromethane and 0.54 ml of triethylamine. The solution was stirred at 23° C. for 30 minutes, cooled to –78° C. and reacted with 0.57 ml of trifluoromethanesulfonyl anhydride, in 0.50 ml of dichloromethane, to form alpha-anomer enriched 2-deoxy-2,2-difluoro-D-ribofuranosyl-3,5-dibenzoyl-1-trifluoromethanesulfonate in solution. Care was taken to maintain the temperature of the reaction mixture below –65° C. The alpha-anomer enriched 2-deoxy-2,2-difluoro-D-ribofuranosyl-3,5-dibenzoyl-1-trifluoromethanesulfonate solution was reacted with the bis-trimethylsilylcytosine solution at 23° C. to form the titled blocked nucleoside which was confirmed by HPLC analysis. The beta to alpha anomeric ratio of the blocked nucleoside was 2.5:1. A quantitative HPLC analysis revealed a yield of blocked beta-anomer nucleoside of 68 percent.

EXAMPLE 11

Preparation of beta-anomer enriched 1-(2'-deoxy-2', 2'-difluoro-3',5'-di-O-benzoyl-D-ribofuranosyl)-4-aminopyrimidin-2-one with 20 equivalents of bis-trimethylsilylcytosine To 5.78 g of cytosine were added 5 ml of dichloromethane, 20.6 ml of N-methyl-N-trimethylsilyl-trifluoroacetamide and 5 ml of dichloromethane to form a homogenous bis-trimethylsilylcytosine solution.

To 1 g of 2-deoxy-2,2-difluoro-D-ribofuranosyl-3,5-dibenzoate was added 3 ml of dichloromethane and 0.55 ml of triethylamine. This solution was stirred at 23° C. for 30 minutes, cooled to –78° C. and reacted with 0.57 ml of trifluoromethanesulfonyl anhydride, in 1 ml of dichloromethane, to form alpha-anomer enriched 2-deoxy-2,2-difluoro-D-ribofuranosyl-3,5-dibenzoyl-1-trifluoromethanesulfonate in solution. Care was taken to maintain the temperature of the reaction mixture below –65° C. The alpha-anomer enriched 2-deoxy-2,2-difluoro-D-ribofuranosyl-3,5-dibenzoyl-1-trifluoromethanesulfonate solution was reacted with the bis-trimethylsilylcytosine solution at 23° C. to form the titled blocked nucleoside which was confirmed by HPLC analysis. The beta to alpha anomeric ratio of the blocked nucleoside was 2.5:1.

To extract the nucleoside product from the reaction mixture, 250 ml of 1N hydrochloric acid were added. The organic layer was separated and washed with 250 ml of 5% sodium carbonate. A quantitative HPLC analysis of the organic layer revealed a yield of blocked beta-anomer nucleoside of 50 percent.

The Table shows the effect the solvent and molar equivalents of pyrimidine nucleoside derivatives have on the anomeric ratio and yield of nucleoside product.

TABLE

| Example | Solvent | (R') Base | (R') Base Equiv | Temp | α/β Nucleoside Ratio | β Yield |
|---|---|---|---|---|---|---|
|  | Dichloromethane | Cytosine | 20 | −25° C. | 1:2.5 | 44% |
| 2 | Dichloromethane | Cytosine | 20 | −30° C. | 1:2.3 | 45% |
| 4 | Dichloromethane | Cytosine | 20 | 0° C. | 1:2.5 | 49% |
| 7 | Dichloromethane | Cytosine | 20 | 23° C. | 1:2.2 | 49% |
|  | Dichloromethane & 1,2 Dichloroethane | Cytosine | 20 | 23° C. | 1:1.8 | 31% |
| 1 | Dichloromethane & 1,2 Dichloroethane | Cytosine | 20 | 23° C. | 1:1.9 | 42% |
| 9 | Dichloromethane & 1,2 Dichloroethane | Cytosine | 20 | 23° C. | 1:2.8 | 50% |
| 10 | Dichloromethane | Cytosine | 20 | 23° C. | 1:2.5 | 68% |
| 3 | Dichloromethane | Cytosine | 20 | −15° C. | 1:2.3 | 58% |
| 6 | Dichloromethane | Cytosine | 20 | 27° C. | 1:2.2 | 54% |
|  | Dichloromethane | Cytosine | 20 | 23° C. | 1:2.2 | 49% |
| 8 | Dichloromethane | Cytosine | 30 | 10° C. | 1:2.7 | 60% |
|  | Dichloromethane | Cytosine | 1.5 | 23° C. | 1:1 | 17% |
|  | Dichloromethane | Cytosine | 3 | 23° C. | 1:1.3 | 6% |
|  | Dichloromethane & 1,2 Dichloroethane | Uracil | 2 | −20° C. | 1:1 | N/D |
|  | Dichloromethane & 1,2 Dichloroethane | Cytosine | 3.5 | −78° C. | 1.3:1 | 10% |
| 5 | Dichloromethane & 1,2 Dichloroethane | N-Acetyl-Cytosine | 10 | −60° C. | 1:2 | 15% |
|  | 1,2 Dichloroethane | Cytosine | 10 | −78° C. | 1:3 | 28% |
|  | Dichloromethane | Cytosine | 10 | 0° C. | 1:2.5 | 32% |
|  | Dichloromethane | 5-F-Uracil | 15 | 23° C. | 1:1 | N/D |

The carbohydrate used to prepare the blocked nucleosides in the table was alpha-anomer enriched 2-deoxy-2,2-difluoro-D-ribofuranosyl-3,5-dibenzoyl-1-trifluoromethanesulfonate. (N/D) means not determined. The yields in Examples 1–11 are based on the amount of carbohydrate and were obtained from a quantitative reverse phase HPLC analysis, wherein the corresponding solution product peak was compared with a standard. The protecting group for the above nucleoside base is trimethylsilyl.

The present invention has been described in detail, including the preferred embodiments thereof. However, it will be appreciated that those skilled in the art, upon consideration of the present disclosure, may make modifications and/or improvements on this invention that fall within the scope and spirit of the invention as set forth in the following claims.

What is claimed is:

1. An alpha-anomer enriched 2,2-difluorocarbohydrate of the formula

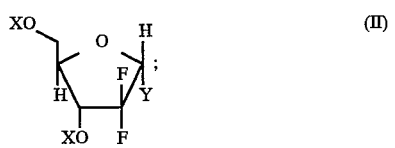

(II)

wherein each X is independently selected from hydroxy protecting groups and Y is selected from the group consisting of trifluoromethanesulfonyloxy, 1,1,1-trifluoroethanesulfonyloxy, octafluorobutanesulfonyloxy and nonafluorobutanesulfonyloxy.

2. An alpha-anomer enriched 2-fluorocarbohydrate of the formula

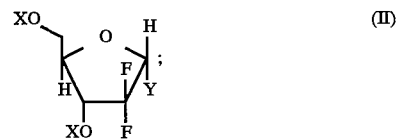

(V)

wherein each X is independently selected from hydroxy protecting groups and Y is selected from the group consisting of trifluoromethanesulfonyloxy, 1,1,1-trifluoroethanesulfonyloxy, octafluorobutanesulfonyloxy and nonafluorobutanesulfonyloxy.

3. A stereoselective process for preparing an alpha-anomer 2,2-difluorocarbohydrate of the formula (II)

wherein each X is independently selected from hydroxy protecting groups and Y is selected from the group consisting of trifluoromethanesulfonyloxy, 1,1,1-trifluoroethanesulfonyloxy, octafluorobutanesulfonyloxy and nonafluorobutanesulfonyloxy; comprising reacting a 2,2-difluorolactol of the formula

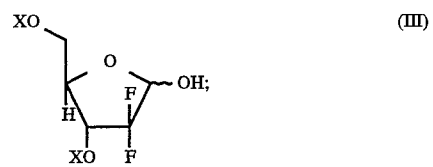

(III)

wherein each X is as defined above; with a base in a low freezing inert solvent; adjusting the temperature of the reaction mixture from about −40° C. to about −120° C.; and adding a sulfonating reagent.

4. The process of claim 3 wherein X is selected from the group consisting of mono-substituted benzoyl, di-substituted benzoyl and benzoyl.

5. The process of claim 3 wherein the base is an amine.

6. The process of claim 5 wherein the amine is selected from the group consisting of triethylamine, trimethylamine, tributylamine, dibutylamine, diethylmethylamine, dimethylethylamine, benzylmethylamine, N-methylmorpholine, tripropylamine, dipropylethylamine, N,N-dimethylbenzylamine, diisopropylethylamine, diethylamine, 1,8 diazabicyclo [5.4.0]undec-7-ene and 1,5-diazabicyclo [4.3.0]-non-5-ene.

7. The process of claim 3 wherein the solvent is selected from the group consisting of dichloromethane, 1,2-dichloroethane, dichlorofluoromethane, acetone, toluene, anisole, chlorobenzene, and mixtures thereof.

8. The process of claim 3 wherein the sulfonating reagent is selected from the group consisting of trifluoromethanesulfonyl anhydride, 1,1,1-trifluoroethanesulfonyl halide, nonaflic acid halide, octaflic acid halide, 1,1,1-trifluoroethanesulfonyl anhydride, nonaflic acid anhydride, and octaflic acid anhydride.

9. The process of claim 5 wherein the amine has a pKa of from about 8 to about 20.

* * * * *